United States Patent [19]

Suzuki

[11] 4,441,374
[45] Apr. 10, 1984

[54] DEVICE FOR DILUTING LIQUID SAMPLE

[75] Inventor: Nobuyoshi Suzuki, Hachioji, Japan

[73] Assignee: Olympus Optical Co. Ltd., Japan

[21] Appl. No.: 433,036

[22] Filed: Oct. 6, 1982

Related U.S. Application Data

[63] Continuation of Ser. No. 195,062, Oct. 7, 1980, abandoned.

[30] Foreign Application Priority Data

Oct. 17, 1979 [JP] Japan .................................. 54-132796

[51] Int. Cl.³ ............................................ G01N 35/00
[52] U.S. Cl. .............................. 73/864.12; 73/864.21; 73/864.22; 422/81
[58] Field of Search ........... 73/864.11, 864.12, 864.21, 73/1 R; 422/81, 82, 100; 436/48, 49, 52, 53, 179; 417/426

[56] References Cited

U.S. PATENT DOCUMENTS

| | | |
|---|---|---|
| 3,234,796 | 2/1966 | Leonards . |
| 3,271,111 | 9/1966 | Boyd, Jr. . |
| 3,552,212 | 1/1971 | Ohlin .................................. 73/864.22 |
| 3,615,234 | 10/1971 | Ludvigsen ............................ 422/82 |
| 3,846,075 | 11/1974 | Coiffi .................................. 73/863.33 |
| 3,935,971 | 2/1976 | Papoff et al. .......................... 417/426 |
| 3,964,988 | 6/1976 | Riseman et al. . |
| 4,108,608 | 8/1978 | Maher, Jr. . |
| 4,204,430 | 5/1980 | Tamm . |

Primary Examiner—S. Clement Swisher
Attorney, Agent, or Firm—Parkhurst & Oliff

[57] ABSTRACT

The disclosed device for diluting liquid sample feeds both the liquid sample and a diluent solution to a mixing point through a first and a second roller pumps respectively, so that the concentration of the liquid sample in the resultant mixture is controlled by regulating the revolving speeds of the first and second roller pumps.

5 Claims, 1 Drawing Figure

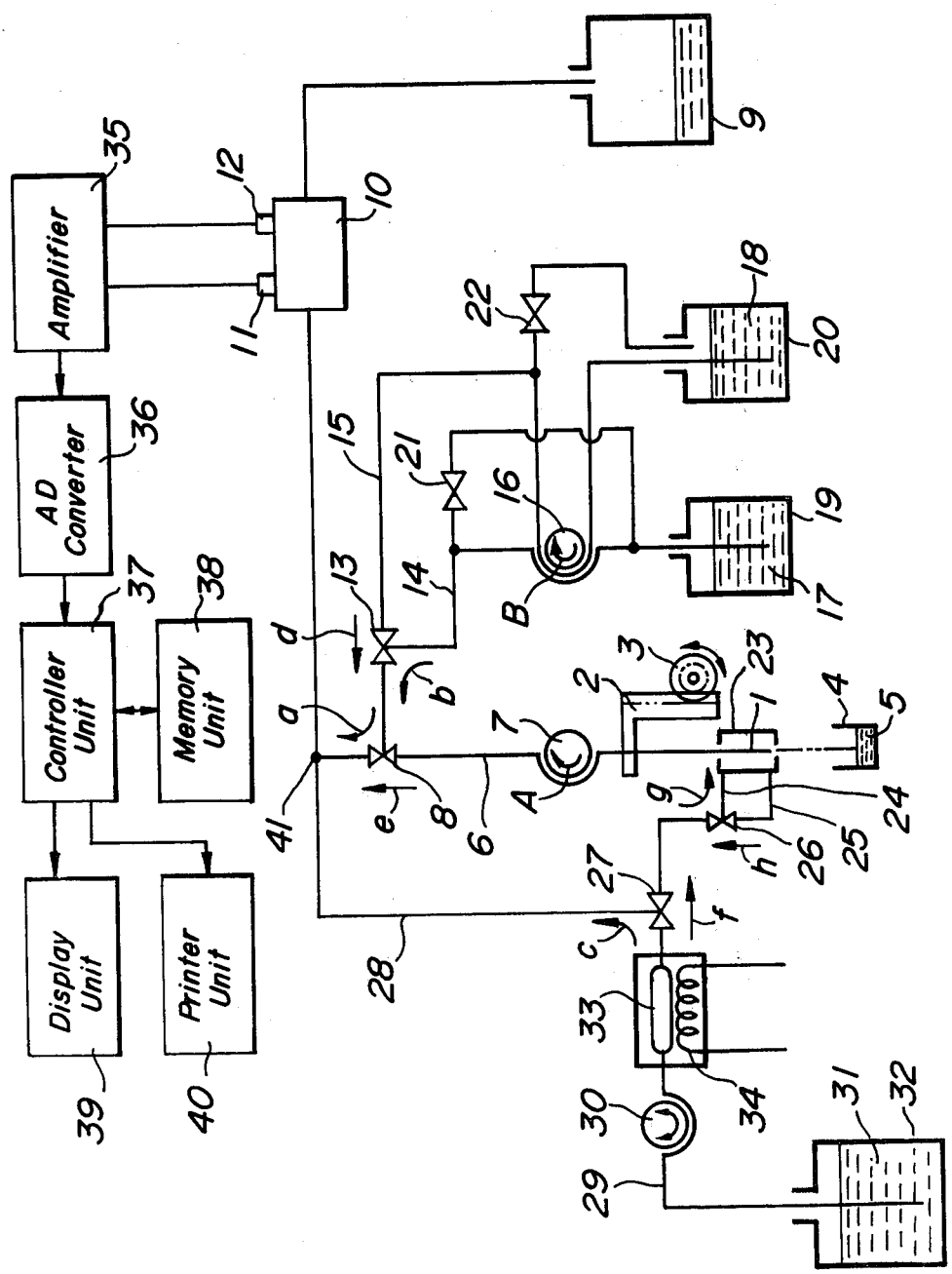

DEVICE FOR DILUTING LIQUID SAMPLE

This is a continuation of application Ser. No. 195,062 filed Oct. 7, 1980 now abandoned.

BACKGROUND OF THE INVENTION

1. Field of the Invention

This invention relates to a device for diluting liquid sample.

2. Description of the Prior Art

In biochemical analyzing devices, such as a device for analyzing ionic concentrations or various ingredients of liquid samples such as serum, the liquid sample is generally diluted at a predetermined rate of dilution before effecting the analysis. As a means for diluting the liquid sample, it has been proposed to use two roller pumps, so that the liquid sample and the diluent solution are sucked by the roller pumps at given rates, respectively, so as to mix the thus sucked liquid sample and the diluent solution and to feed the mixture to a flow-cell or reaction vessel at a predetermined position. The device for diluting liquid sample of the prior art, however, uses a fixed ratio of revolving speeds for the two roller pumps, and the rate of dilution is determined by a ratio of diameters of tubes constituting the roller pumps. Thus, the device of the prior art has shortcomings in that the rate of dilution cannot be selected at will and that, if the rate of dilution is unintentionally changed by replacement of a worn-out tube with a new tube, correction for such change is extremely difficult.

SUMMARY OF THE INVENTION

Therefore, an object of the present invention is to obviate the aforementioned shortcomings of the prior art, by providing an improved device for diluting liquid sample which is so constructed that the rate of dilution of the liquid sample can be modified as desired in an easy and accurate fashion.

The present invention provides a device for diluting liquid sample comprising a first roller pump to suck and feed the liquid sample, a second roller pump to suck and feed a diluent solution, a liquid path tubing including branch path tubes connected to outputs of said first and second roller pumps and liquid path tubes to feed the liquid sample and the diluent solution thus sucked and fed to a predetermined position, and a means to regulate ratio of revolving speeds of said first and second roller pumps so as to control rate of dilution of said liquid sample by said diluent solution.

BRIEF DESCRIPTION OF THE DRAWING

For a better understanding of the invention, reference is taken to the accompanying drawing, in which:

The single drawing is a schematic diagram showing the construction of an ionic concentration measuring apparatus including an example of the device for diluting liquid sample according to the present invention.

In the drawing, 1 is a nozzle, 2 is a rack, 3 is a pinion gear, 4 is a vessel, 5 is a liquid specimen (liquid sample), 6, 14, 15, 24, 25, 28, 29 are liquid path tubes, 7, 16, 30 are roller pumps, 8, 13, 26, 27 are cross valves, 9 is an exhaust vessel, 10 is a cell, 11 is a reference electrode, 12 is an ion sensor, 17 is a first standard solution, 18 is a second standard solution, 19 is a first standard solution vessel, 20 is a second standard solution vessel, 21, 22 are valves, 23 is a cylindrical member, 31 is a diluent solution, 32 is a diluent solution vessel, 33 is a liquid reservoir, 34 is a heat exchanger, 35 is an amplifier, 36 is an AD converter, 37 is a controller unit, 38 is a memory unit, 39 is a display unit, 40 is a printer unit, and 41 is a joint portion.

DETAILED DESCRIPTION OF THE PREFERRED EMBODIMENT

The accompanying single drawing illustrates a schematic diagram if a so-called through-flow type ionic concentration measuring apparatus including a device for diluting liquid sample according to the present invention, wherein the liquid sample (to be referred to as "liquid specimen", hereinafter) is fed to a flow cell at a predetermined rate of dilution, which flow cell has a reference electrode and an ion sensor selectively sensitive to specific ions, so as to determine the concentrations of the specific ions in the liquid specimen. A nozzle 1 for sucking the liquid specimen is detachably mounted to one end of a rack 2 which is vertically movable. The rack 2 meshes a pinion 3 fixed to the output of a motor (not shown) so as to selectively rotate in either direction as shown by the two-way arrow in the drawing. The nozzle 1 can be selectively lowered by turning the pinion 3 in a proper direction through the motor (not shown) and the rack 2, until the nozzle 1 comes into liquid specimen 5 held by a liquid specimen vessel 4. A liquid path tube 6 has one end thereof connected to the nozzle 1 and the opposite end thereof connected to an exhaust vessel 9 through a roller pump 7 and a cross valve 8, which roller pump 7 is selectively driven in the direction of the arrow A of the drawing. A cell 10 is disposed on the liquid path tube 6 at a position between the cross valve 8 and the exhaust vessel 9, and a reference electrode 11 and an ion sensor 12 are mounted on the cell 10 in such a manner that a liquid-contact portion and an ion-sensing portion thereof come in contact with the liquid fed into the cell 10.

The ion sensor 12, for instance, includes an insulated-gate type transistor which has been developed in recent years. This ion sensor is made by coating one or more electrically-insulating ion-sensitive membranes to the gate portion of a field effect transistor, which membranes selectively sense specific ions such as those of silicon oxide ($SiO_2$) and silicon nitride ($Si_3N_4$). The semi-conductor substrate of the field effect transistor may have only one coating of an ion-sensitive membrane sensitive to specific one kind of ion or a plurality of coatings of ion-sensitive membranes sensitive to different kinds of ions respectively, by having a plurality of insulated gate portions thereon. The aforementioned field effect transistor, with one or more ion-sensitive membranes, can be easily manufactured by a process commonly used by those skilled in the art of semi-conductor devices, and such field effect transistor has advantages of long service life and small size. In the illustrated embodiment of the present invention, three kinds of ions, i.e., $Na^+$, $K^+$, and $Cl^+$, are substantially simultaneously measured by using the aforementioned semi-conductor ion sensor.

The remaining inlet of the cross valve 8 is connected to another cross valve 13. The remaining two inlets of the cross valve 13 are connected to first and second standard solution vessels 19 and 20 holding first and second standard solutions 17 and 18 with known ion concentrations respectively, through liquid path tubes 14 and 15 and a roller pump 16 selectively rotatable in the direction of the arrow B of the drawing. The liquid path tubes 14 and 15 are branched at positions between the cross valve 13 and the roller pump 16, so that the thus branched paths are led to the first and second standard solution vessels 19 and 20 through valves 21 and 22 respectively.

A cylindrical member 23 is fixed near the nozzle 1 in such a manner that, when the nozzle 1 is at its top dead center position, the cylindrical member 23 encloses at least that portion of the nozzle 1 which is to come into the liquid specimen. The nozzle 1 moves along the longitudinal axis of the cylindrical member 23. The upper and lower ends of the cylindrical member 23 are connected to liquid path tubes 24 and 25, and the opposite ends of the liquid path tubes 24 and 25 are connected to a cross valve 26. The remaining inlet of the cross valve 26 is connected to another cross valve 27, and one of the remaining two inlets of the cross valve 27 is connected to one end of a liquid path tube 28. The opposite end of the liquid path tube 28 is connected to a joint portion 41 of the liquid path tube 6 at a position between the cross valve 8 and the cell 10.

The last inlet of the cross valve 27 is connected to one end of a liquid path tube 29, whose opposite end is connected to a diluent solution vessel 32 holding diluent solution 31 through a roller pump 30, which pump 30 is selectively rotatable in either direction as shown by the two-way arrow of the drawing. A liquid reservoir 33 is formed on the liquid path tube 29 between the roller pump 30 and the cross valve 27. A heat exchanger 34 is disposed in the liquid reservoir 33, so as to keep the diluent solution drawn by the roller pump 30 at a desired temperature.

On the other hand, the output signals such as output voltages from the reference electrode 11 and the ion sensor 12, representing the ionic concentration of the liquid specimen sensed thereby, are applied to a controller unit 37 such as a computer through an amplifier 35 and an AD converter 36. The controller unit 37 applies predetermined operational processing on the output signals based on a calibration line (function of the voltages and the ion concentration) pre-stored in a memory unit 38. The outcome of the processing at the controller unit 37 can be shown on a display unit 39 or printed by a printer unit 40 as a final output. The calibration line is set by feeding the first and second standard solutions 17 and 18 into the cell 10 together with the diluent solution 31, measuring the liquid in the cell 10 to produce output voltages, and storing the output signals in the memory unit 38. The controller unit 37 applies operational processing on the calibration line to produce the function between the voltages and the ion concentration, which function is stored in the memory unit 38.

In the illustrated embodiment, the ratio between the revolving speed of the roller pump 30 in the counter-clockwise direction and the revolving speed of the roller pump 7 can be regulated as desired.

The operation of the illustrated ion concentration measuring apparatus will now be described.

The setting of the calibration line will be described at first. The cross valve 8 is set in the direction of the arrow a, the cross valve 13 is set in the direction of the arrow b, and the cross valve 27 is set in the direction of the arrow c, and the valve 21 is closed while the valve 22 is opened. The roller pump 16 is rotated in the direction of the arrow B by a predetermined number of revolutions while the roller pump 30 is rotated in a counter-clockwise direction by a predetermined number of revolutions, and a predetermined ratio of revolving speeds is kept between the roller pump 16 and the roller pump 30 during the aforesaid revolutions. The diluent solution 31 kept at a predetermined temperature by the heat exchanger 34 is now mixed with the first standard solution 17 at the joint portion 41 between the liquid path tubes 6 and 28, so as to produce the desired rate of dilution. The thus diluted first standard solution 17 is fed into the cell 10, where the voltages corresponding to the concentrations of $Na^+$, $K^+$, and $Cl^+$ therein are measured and stored in the memory unit 38. In this case, the second standard solution 18 is also pumped up by the rotations of the roller pump 16, but the then open valve 22 feeds back the pumped second standard solution 18 back to the second standard solution vessel 20. Then, the cross valve 13 is reset to the direction of the arrow d, and the valve 21 is opened while the valve 22 is closed. The roller pumps 16 and 30 are rotated in the same directions as before by predetermined numbers of revolutions respectively, while maintaining a preset ratio of revolving speeds therebetween. Whereby, the second standard solution 18 is diluted at a desired rate and fed into the cell 10, wherein the voltages corresponding to the concentration of $Na^+$, $K^+$, and $Cl^+$ therein are measured and stored in the memory unit 38. In this case, the first standard solution 17 is also pumped up by the rotation of the roller pump 16, but the then open valve 21 feeds back the pumped first standard solution 17 back to the first standard solution vessel 19. The controller unit 37 sets or determines the calibration line for each ion based on the stored voltage for that ion in the first and second standard solutions 17 and 18, and the thus determined calibration line is stored in the memory unit 38. After the calibration line is set, various valves and the roller pumps 16, 30 operates in the same manner as that during the ionic concentration measurement for the first standard solution 17, and the first standard solution dilutes at the desired rate is placed at least in the cell 10 for keeping the reference electrode 11 and the ion sensor 12 as dipped in the first standard solution 17. Whereby, the preparation for measuring the ionic concentration of the liquid specimen is completed.

To measure the ionic concentration of the liquid specimen, the pinion gear 3 is turned in a counter-clockwise direction as seen in the drawing by driving a motor (not shown), to move the nozzle 1 through the rack 2 until the nozzle 1 comes into the liquid specimen 5. Then, the cross valve 8 is set in the direction of the arrow e, and the roller pump 7 is rotated in the direction of the arrow A by a predetermined number of revolutions while the roller pump 30 is rotated in a counter-clockwise direction as seen in the drawing by a predetermined number of revolutions, with the ratio of the revolving speeds of the roller pumps 7 and 30 kept at a preset value. After a predetermined amount of the liquid specimen 5 and a predetermined amount of the diluent solution 31 are pumped up in this way, the pinion gear 3 is turned in a clockwise direction as seen in the drawing to store the nozzle 1, especially that portion which was in the liquid specimen before, in the cylindrical member 23 (as shown in the drawing), and the roller pumps 7 and 30 are rotated at a predetermined ratio of revolving speeds to mix the thus pumped liquid specimen 5 with the diluent solution 31 at the joint portion 41 for diluting the liquid specimen 5 at a desired rate of dilution. Thus, the diluted liquid specimen is fed into the cell 10, where the ion sensor 12 detects voltages representing concentrations of $Na^+$, $K^+$, and $Cl^+$ in the liquid specimen 5 as diluted at the desired diluting rate. The controller unit 37 processes the voltages thus detected based on the corresponding calibration line stored previously in the aforesaid manner. The processed result is shown on the display unit 39 and printed by the printer unit 40 as the final output.

After measuring the ionic concentration of the liquid specimen 5, the cross valves 27 and 26 are reset in the directions of the arrows f and g, respectively, and the roller pump 30 is rotated in a counter-clockwise direction as seen in the drawing, to feed the diluent solution 31 to the inside of the cylindrical member 23 through the liquid path tube 29, the cross valves 27, 26 and the liquid path tube 24, so as to wash the outside surface of the nozzle 1. At the same time, the roller pump 7 is rotated in the direction of the arrow A at a higher speed than that of the roller pump 30. Accordingly, the diluent solution 31 fed into the cylindrical member 23 by the roller pump 30 is pumped up by the roller pump 7 along the outside surface of the nozzle 1 without dropping down from the bottom opening of the cylindrical member 23, and is sucked to the inside of the nozzle 1 and drained into the exhaust vessel 9 through the inside of the nozzle 1, the liquid path tube 6, and the cell 10. In this process, cleaning or washing is carried out on the inside and outside surfaces of the nozzle 1, the liquid path tube 6, the cell 10 and the reference electrode 11 with the ion sensor 12 carried by the cell 10. The roller pumps 7 and 30 cease their operations after forcing a predetermined amount of the diluent solution 31 through the nozzle 1, the liquid path tube 7, and the cell 10. Just before the roller pump 7 comes to rest, the roller pump 30 rotates in a clockwise direction as seen in the drawing and the cross valve 26 is reset in the direction of the arrow h, so as to return the diluent solution 31 in the cylindrical member 23 to the diluent solution vessel 32 through the liquid path tube 25, the cross valves 26, 27 and the liquid path tube 29. Thus, when both of the two roller pumps 7 and 30 come to rest, an air layer is formed at the tip of the nozzle 1.

Then, various valves and the roller pumps 16 and 38 are operated in the same manner as that for the measurement of the ionic concentration of the first standard solution 17, so as to pump up and feed the first standard solution 17 of the predetermined rate of dilution into at least the cell 10. Whereby, the aforementioned state of being ready for measuring the ionic concentration of the liquid specimen is established.

Similarly, the ionic concentrations of other liquid specimens can be measured in succession by repeating the aforesaid process. It is noted here that the controller unit 37 can be also used for controlling, for instance, the motor (not shown) to drive the pinion gear 3, the roller pumps 7, 16, 30, the cross valves 8, 13, 26, 27, and the valves 21, 22.

With the ionic concentration measuring apparatus of the aforementioned construction, under the conditions ready for measuring the liquid specimen 5, the inside space of the cell 10 is always filled with the first standard solution 17, so that the reference electrode 11 and the sensor 12 are protected against deterioration of their operating characteristics and durabilities. Besides, the measurement of the liquid specimens can be started quickly. Furthermore, the contaminations between different liquid specimens 5 and between the liquid specimen 5 and the diluent solution 31 or the first standard solution 17 are effectively prevented by forcing a predetermined amount of the diluent solution 31 through the inside and outside surfaces of the nozzle 1, the liquid path tube 6 and the cell 10 after each measurement of the ionic concentration of the liquid specimen 5, by removing the residual diluent solution 31 on the outer surface of the nozzle 1 through the reverse rotation of the roller pump 30, and by forming an air layer at the tip of the nozzle 1. The provision for selective pump up of either one of the two, i.e., the first and the second, known standard solutions 17 and 18 with different ionic concentrations into the cell 10 makes it possible to redraw the calibration line at any time or at preset times as determined by a program. Since the cell 10 is filled with the first standard solution 17 during the state ready for measuring the liquid specimen, the preset calibration line can be corrected before starting the measurement of the liquid specimen, by measuring the thus filled first standard solution 17 either before each measurement of the liquid specimen or at predetermined cyclic intervals. Whereby, accurate measurement can be always ensured. As the revolving speed of each roller pump is controllable and as the ratio of revolving speeds between the roller pump 30 and the roller pump 7 and between the roller pump 30 and the roller pump 16 are used for determining the rate of dilution of the liquid specimen 5 and the first and second standard solutions 17 and 18, any desired rate of dilution can be easily and accurately set for each liquid specimen or for each item of measurement, for instance by applying a control signal to the control means 37 from the outside. Of course, means may be provided for regulating the ratios of the revolving speeds of the pumps. Accordingly, each item of measurement can be measured at the most suitable rate of dilution, and the measuring range at the measuring portion can be widened by modifying the rate of dilution. Moreover, when any tube constituting an essential part of each roller pump is replaced, variation of the rate of dilution caused by such replacement can be easily corrected in the device of the present invention.

It should be understood that the present invention is not restricted to the aforementioned example, and many changes and modifications thereof are possible. For instance, although the illustrated embodiment uses the nozzle 1 which is vertically movable relative to the fixed cylindrical member 23, the relation can be reversed by making a cylindrical member 23 vertically movable relative to a fixed nozzle 1. In this case, when the cylindrical member 23 is at its raised position, the liquid specimen vessel 4 may be raised until the nozzle 1 enters into the liquid specimen 5, so as to allow suction of the liquid specimen. The present invention can be applied not only to the ionic concentration measurement, but also to analysis of various components of the liquid specimen 5 by colorimetric measurement of the liquid specimen 5 in the cell 10. The present invention can be also applied to a process in which the liquid specimen of a predetermined rate of dilution is poured into a reaction vessel so as to carry out the necessary measurement in the reaction vessel.

What is claimed is:

1. A device for diluting liquid sample comprising a first roller pump to suck and feed a liquid sample, a second roller pump to suck and feed a diluent solution, a liquid path tubing including a branch connected to outputs of said first and second roller pumps to feed the liquid sample and diluent solution thus sucked and fed to a predetermined position, and means to regulate a ratio of revolving speeds of said first and second roller pumps to control a rate of dilution of said liquid sample by said diluent solution, the improvement comprising a third roller pump having inputs connected to a plurality of standard solutions and outputs selectively connectable to said liquid path tubing, whereby a ratio of revolving speeds of said second and third roller pumps is changed to control a rate of dilution of one of said standard solutions by said diluent solution, wherein between the outputs of the third roller pump and said liquid path tubing is arranged a first valve having inputs connected to the outputs of the third roller pump and an output connected to the liquid path tubing.

2. A device according to claim 1, wherein between said first roller pump and the liquid path tubing is arranged a second valve having inputs connected to the first roller pump and the output of said first valve and an output connected to the liquid path tubing.

3. A device according to claim 1, comprising circulating liquid path tubes provided from junction points between the outputs of the third roller pump and the inputs of the first valve to the inputs of the third roller pump, and a third valve arranged in each circulating liquid path tube.

4. A device according to claim 1, further comprising circulating liquid path tubes arranged from junction points between the outputs of the third roller pump and the standard solution containers, and a third valve provided in each circulating liquid path tube.

5. A device according to claim 1, further comprising a nozzle wherein an input of the first roller pump is connected to said nozzle to be immersed into the liquid sample, a driving member for moving the nozzle up and down, a cylindrical member through which said nozzle moves, a diluent solution path tube having one end connected to the output of the second roller pump through a fourth valve and the other end connected to the cylindrical member, and said nozzle is washed by simultaneously operating said first and second roller pumps to cause diluent solution to flow from the second roller pump, through said diluent solution path, the cylindrical member, the nozzle and the first roller pump.

* * * * *